(12) United States Patent
Gülzow et al.

(10) Patent No.: US 9,040,293 B2
(45) Date of Patent: May 26, 2015

(54) CELL CULTURE DISH

(75) Inventors: Nico Gülzow, Hamburg (DE); Thomas Reimann, Geesthacht (DE); Jochen Beese, Norderstedt (DE); Ute Kowanz, Hamburg (DE); Yvonne Radacz, Schwäbisch Gmünd (DE)

(73) Assignee: Eppendorf AG, Hamburg (DE)

( * ) Notice: Subject to any disclaimer, the term of this patent is extended or adjusted under 35 U.S.C. 154(b) by 726 days.

(21) Appl. No.: 12/715,822

(22) Filed: Mar. 2, 2010

(65) Prior Publication Data

US 2011/0003376 A1    Jan. 6, 2011

(30) Foreign Application Priority Data

Mar. 9, 2009    (DE) .......................... 10 2009 013 673

(51) Int. Cl.
 C12M 1/22    (2006.01)
 C12M 3/00    (2006.01)
 C12M 1/00    (2006.01)
 B01D 27/00   (2006.01)
 B01D 35/00   (2006.01)
 B01D 35/28   (2006.01)

(52) U.S. Cl.
 CPC ..................................... *C12M 23/10* (2013.01)

(58) Field of Classification Search
 CPC ....................................................... C12M 23/10
 USPC .............................. 435/283.1–309.4; 210/445
 See application file for complete search history.

(56) References Cited

U.S. PATENT DOCUMENTS

| 3,055,808 A | | 9/1962 | Henderson | |
|---|---|---|---|---|
| 3,158,553 A | | 11/1964 | Carski | |
| 3,203,870 A | * | 8/1965 | Andelin | 435/305.4 |
| 3,248,302 A | | 4/1966 | Mackin | |
| 3,649,463 A | | 3/1972 | Buterbaugh | |
| 4,675,298 A | * | 6/1987 | Brusewitz | 435/305.1 |
| 5,520,302 A | | 5/1996 | Anderson et al. | |
| 6,472,203 B1 | * | 10/2002 | Gallup et al. | 435/309.1 |
| 2003/0057148 A1 | * | 3/2003 | Zuk, Jr. | 210/445 |
| 2005/0089997 A1 | * | 4/2005 | Minton | 435/288.3 |
| 2007/0166819 A1 | * | 7/2007 | Ghosh et al. | 435/305.4 |

FOREIGN PATENT DOCUMENTS

| DE | 1 940 202 | 6/1966 |
|---|---|---|
| DE | 10 2007 027273 A1 | 11/2008 |
| GB | 2106083 | 4/1983 |
| JP | 2005312317 A | 11/2005 |

* cited by examiner

*Primary Examiner* — Nathan Bowers
*Assistant Examiner* — Lydia Edwards
(74) *Attorney, Agent, or Firm* — Vidas, Arrett & Steinkraus

(57) ABSTRACT

A cell culture dish, comprising: a dish with a bottom wall and a circumferential side wall standing upward from the same, a lid, which sits sealingly on the side wall in an aeration position, and means for holding the lid on the dish above the sealing position in an aeration position in which there is an aeration gap between side wall and lid, wherein these means are adapted to be overcome by pressing the lid and the dish together in order to bring the lid from the aeration position into the sealing position.

11 Claims, 6 Drawing Sheets

CELL CULTURE DISH

CROSS-REFERENCE TO RELATED APPLICATIONS

Figures 1, 2, 3:
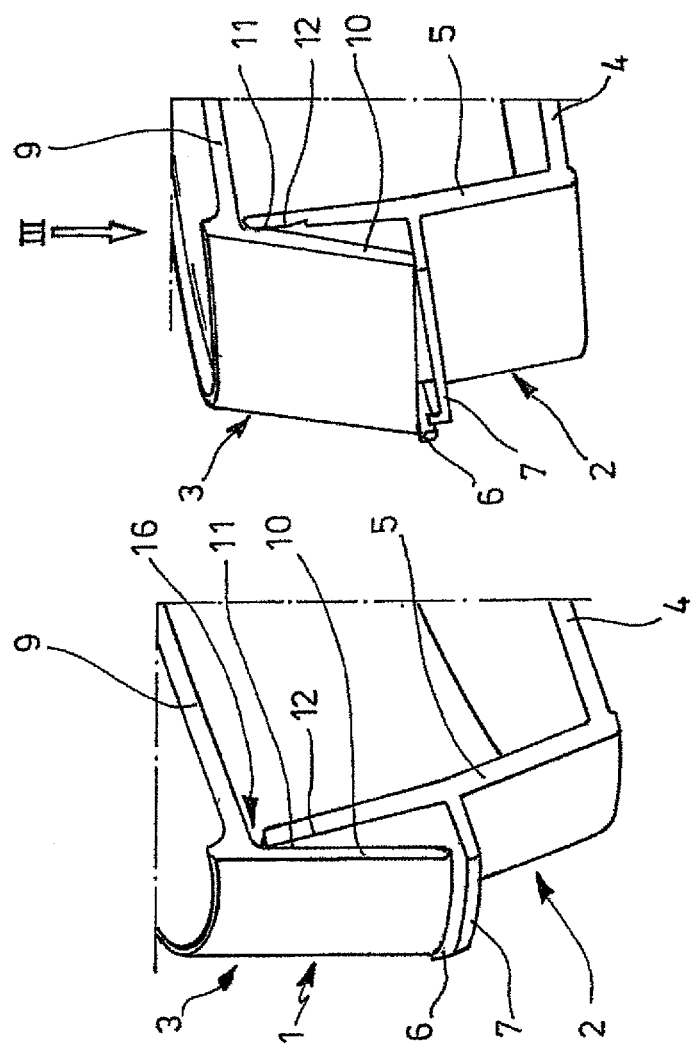

Not applicable.

STATEMENT REGARDING FEDERALLY SPONSORED RESEARCH

Not applicable.

BACKGROUND OF THE INVENTION

The present invention is related to a cell culture dish.

Cell culture dishes are dishes with a lid, which are used in the biological or medical laboratory for cell culture and in order to cultivate micro-organisms (microbes and fungi) and higher cells (for instance, mammalian cells, cell tissue etc.). In a round, transparent realisation they are also designated as Petri dishes.

U.S. Pat. No. 3,055,808, the entire contents of which is incorporated herein by reference, discloses a Petri dish for the cultivation of micro-organisms in particular, comprising a flat cylindrical dish and a lid. The dish has an upper lateral edge, extending circumferentially and sealing the lid. The cup-shaped lid has the same shape, but a greater diameter, so that it fits slackly to the dish. At one corner between a covering wall and a circumferential side wall, the lid has a pressure sensitive, permanently tacky adhesive for detachably fastening the lid on the dish and for hermetically sealing the connection between lid and dish. The adhesive extends in the circumferential direction along the upper edge of the dish and along the inner surfaces of the perimeter of the covering wall at the corner. The lid is made of a flexible material, which is realised such that it bends when a lateral pressure is applied to its side wall, and consequently the seal between the lid and the dish is released, the adhesive remaining on the lid when the lid is removed from the dish.

The Petri dish serves for the culture of micro-organisms, of bacteria in particular. The Petri dish is hermetically closed when the lid is put on. The lid has no aeration position. An increased contamination through microbial growth might occur when the adhesive is applied, so that the expense for sterilisation is increased. The tacky property of the adhesive may be altered by a long storage time, increased temperature in the incubator, influence of low temperatures or contact with culture medium. Through this, the sealing between the lid and the dish may be compromised. Also, ingredients of the adhesive may contaminate the culture medium.

The company BD Biosciences, San Jose, USA offers Petri dishes having a diameter of 50 mm and a height of 9 mm under the designation "BD Falcon" and with the article number 35106. The Petri dishes are made of polystyrene and have a lid that has a sealing seat on the dish. For this purpose, the dish has a conical sealing seat on the upper edge of a circumferential side wall, and the lid has a complementary sealing seat on the inner wall of a lid side wall. The lid is adapted to be clampingly seated onto the sealing seat of the dish, i.e. there is a frictional connection as soon as the lid is put up. In this, the length of the side wall of the lid does not exceed the conical region of the side wall of the dish. The complementary sealing seat is a result of this, but no lever action can deform the lid when it is opened. The Petri dish has no defined aeration position with an aeration gap between lid and dish. Once the lid is sealingly put on, this Petri dish cannot be opened in a simple way, but an increased expenditure of force has to be applied for this task instead. It is not possible to handle this Petri dish by one hand only, in particular not when opening it. In order to overcome the frictional connection, the user must take the Petri dish at the lower dish with one hand and hold it fast, and with the other hand he must strongly pull upward the lid of the Petri dish. In such a handling it is unavoidable that turbulences arise in the culture medium in the Petri dish, by which sensible cells, manipulated cells in particular (for instance transformed and/or infected cells etc.), can be influenced negatively, for instance they detach from the bottom of the dish, and thus become useless. In addition, these turbulences are accompanied by formation of droplets/aerosols like a drizzle, so that a drizzle/aerosol of culture medium is burst into the air of the surroundings and contaminates the same when the Petri dish is opened. This is dangerous and thus undesired in the cultivation of pathogenic organisms in cells (viruses, mycoplasma, prions etc.) or of cells which excrete a toxin into the culture medium, because the user is exposed to a health hazard by this.

For incubating or cultivating, respectively, cells or micro-organisms respectively are introduced into a cell culture dish. In a common procedure, the dish is covered up by putting up a slackly sitting lid in order to protect the cells or micro-organisms, respectively. The cell culture dish is set into an incubator in which optimum conditions for the incubation or cultivation respectively are generated by adjusting an atmosphere and temperature that is suited for this. The atmosphere in the cultivator is normally formed by air having a certain content of $CO_2$ and $O_2$ in a certain air humidity. The slackly laying lid permits the atmosphere present in the incubator to be present also within the cell culture dish, i.e. on the cells or micro-organisms, respectively. Moreover, cell culture dishes are known wherein the lid has a greater distance from the dish by punctual knobs, so that the gas exchange with the interior of the cell culture dish is more markedly.

From U.S. Pat. No. 5,520,302, the entire contents of which is incorporated herein by reference, a rectangular Petri dish for cultivating micro-organisms is known. It has a rectangular dish with a bottom wall and a circumferential side wall, which projects upward from the bottom wall. Further, the cell culture dish has a rectangular lid, which is adapted to be mounted in two different positions. The lid has a covering wall and a circumferential exterior as well as a circumferential interior lid side wall, both extending downward from the covering wall and limiting an endless groove. The contour of the endless groove corresponds to the upper end of the side wall of the dish. When the lid completely covers up the dish in a first position, the upper end of the side wall is prevented from engaging completely into the groove, so that no passage of gas between lid and dish would be possible. However, in case that the lid is positioned completely above the dish in a second position, being turned about 180°, the upper end of the side wall engages completely into the groove. Passage of gas between lid and dish is prevented through this.

In the known Petri dish, the lid has to be put onto the dish in the correct alignment in order to permit the passage of gas between lid and dish. For gas-tight closure of the Petri dish, the lid has to be taken off and put up anew after rotating it about 180°. Handling the Petri dish is made more difficult through this. Moreover, the micro-organisms may be contaminated in these manipulations. Further, the atmosphere in the interior of the Petri dish can adapt itself to the composition of the surroundings when the lid is reset, so that the culture conditions in the interior of the Petri dish are not preserved any more.

U.S. Pat. No. 4,675,298, the entire contents of which is incorporated herein by reference, discloses a Petri dish with a circular lower dish and a lid that is slackly disposed thereon. Projections are disposed on the perimeter of the inner side of the lid, and indentations matching the same are formed on the edge of the dish. This permits to adjust a gap between the lid and the dish in order to control the gas exchange between the interior of the Petri dish and the atmosphere. In order to adjust the gap, the lid must be rotated with respect to the dish, which necessitates using both hands. For this purpose, the user has to take the Petri dish out of an incubator at first, as the case might be. Because the lid sits slackly on the dish, the Petri dish is not liquid-tight, even when the gap between dish and lid is closed completely. Due to this, spillage of culture medium or micro-organisms, respectively, might occur in the manipulation of the Petri dish.

Starting from this, the present invention is based on the objective to provide a more user-friendly Petri dish. With user-friendly is to be understood in particular: simple manual and/or automatic handling (repeatable opening, repeatable closing and/or carrying the cell culture dish) with only one hand or an automatic tool, respectively. Moreover, the term "user friendly" is intended to mean also low-risk with respect to potential contamination of the user, i.e. the risk of the user to be exposed to contaminated (infected or toxic) culture medium is minimised.

BRIEF SUMMARY OF THE INVENTION

The cell culture dish according to the present invention comprises: a dish with a bottom wall and a circumferential side wall standing upward from the same, a lid, which sits sealingly on the side wall an in aeration position, and means for holding the lid on the dish above the sealing position in an aeration position in which there is an aeration gap between side wall and lid, wherein these means are adapted to be overcome by pressing the lid and the dish together in order to bring the lid from the aeration position into the sealing position.

In the cell culture dish of the present invention, the dish can be covered up by putting up the lid after the introduction of cells or micro-organisms. The lid can be disposed in the aeration position at first, in which the aeration gap connects the interior of the cell culture dish with the surroundings. In this, the lid can be put on the dish in arbitrary positions. The user needs only one single hand for doing this. In this configuration, the cell culture dish can be put into an incubator so that the interior of the cell culture dish is connected with the atmosphere in the incubator via the aeration gap, and this atmosphere is applied to the cells or micro-organisms in the dish. After the incubation or cultivation, for instance when the cell culture dish is to be removed from the incubator, the cell culture dish can be tightly closed by pressing lid and dish together. The sealing position is accomplished by this, in which the lid sits sealingly on the side wall. This sealing seat makes sure that culture liquid swashing up in the transportation does not leak out of the cell culture dish. Further, the sealing seat makes sure that the atmosphere adjusted in the incubator remains preserved in the cell culture dish for a longer time or changes more slowly than if the lid would be disposed in the aeration position.

The present invention incorporates possible embodiments which satisfy increased tightness demands. The demands may be, for instance, to be liquid-tight in that sense that no liquid leaks out when a column of the culture liquid stands in the cell culture dish at the sealing region between lid and side wall. Further, embodiments are possible in the frame of the present invention in which the lid closes the dish so as to be gas-tight. In a simpler embodiment, this gas-tight closure may be given when there is equal gas pressure within and outside of the cell culture dish. In an embodiment satisfying further increased demands, gas-tightness is also given when there are different pressures within and outside of the cell culture dish (for instance pressures differing about 0.2 bar or 0.5 bar). Gas-tightness may also be achieved in that the user purposefully incorporates a film of liquid into the sealing region between dish and lid. For instance, this may be performed in that the user "swashes in" a part of the culture medium brought into the cell culture dish into the sealing region. The user may attain this by a slight tumbling movement or swivelling movement, respectively, of the cell culture dish.

For tightly closing the cell culture dish, the lid has only to be pressed faintly against the dish that is disposed on a subsoil or held in the hand. By this, the aeration gap is closed and the lid sits sealingly on the side wall. Any preliminary changeover of the lid is not necessary. Thus, the user can close the dish by merely pushing the lid down onto the dish that is disposed on a subsoil. Even for this, he/she needs only one single hand or only one finger, respectively. As a consequence of this, he/she can close the cell culture dish easily still within an incubator. Through this it is avoided on the one hand that liquid can leak out in the transportation. And on the other hand, it is avoided that the atmosphere inside the cell culture dish adapts itself to the atmosphere prevailing outside of the incubator, that is to say, the original incubator atmosphere is preserved inside the cell culture dish even though the same is no more located in the incubator. In particular, a loss of $CO_2$ can be avoided, so that a constant pH can be maintained in the cell culture dish for a longer time. This is made sure in particular when the user purposefully brings a film of liquid into the sealing region. The risk of contamination of cells or micro-organisms, respectively, when arranging the lid into the aeration position and the sealing position is reduced. Swashing over or leaking out, respectively, of culture medium from the cell culture dish can be avoided in the sealing position. Thus, a risk for the user to be exposed to contaminated medium is reduced also. Altogether, the cell culture dish of the present invention has more favourable utilisation conditions than the state of the art that was mentioned in the beginning.

The lid can be arranged detachably on the dish in the sealing position or the aeration position, respectively, in order to be able to take the lid off from the dish and to have access to the cells or micro-organisms, respectively, in the dish. The bottom area of the cell culture dish of the present invention can be shaped differently, in particular as being rectangular, oblong or circular. It is preferably circular.

The means for holding the lid on the dish in the aeration position can be realised differently. For instance, it may be dealt with a catch which is effective between lid and dish in the aeration position, can be released by pressing lid and dish further together and arrives in a further catch position in the sealing position, as the case may be. The catch may be realised reversibly, in order to detach the lid from the dish if need be.

According to one embodiment, the means for holding have at least one resilient supporting element between lid and dish. In the aeration position, lid and dish support each other via the resilient supporting element. In the aeration position, lid and dish are pressed together, making use of the resilient property of the resilient supporting element. The resilient supporting element facilitates handling by permitting to cover up the dish in a conventional manner by merely putting up the lid.

The resilient supporting element may be existing on the lid or on the dish. According to a preferred embodiment, it exists on the dish. The resilient supporting element can be disposed at different position of the dish. For instance, it may stand upward from the bottom wall of the dish within or outside of the circumferential side wall, or project from the upper edge of the side wall. According to a preferred embodiment, the side wall of the dish has at least one laterally projecting resilient supporting element, and the lid has a lid side wall that projects downward from a covering wall and is adapted to be put on the supporting element.

In principle, the supporting element can project into the interior of the dish from the inner side of the side wall, the lid side wall then engaging into the dish. According to a preferred embodiment, the supporting element projects from the outer side of the side wall and the lid side wall grips over the side wall of the dish. In this embodiment, carry-over of contaminations over the lid side wall into the dish is avoided.

The present invention incorporates embodiments in which the aeration gap is shaped irregularly. For instance, starting from a seating region in which the lid sits on the side wall in the aeration position, the aeration gap between lid and side wall can increase with increasing distance from this seating region. Such an embodiment needs only one single resilient supporting element. According to a preferred embodiment, the dish has resilient supporting elements on opposing sections of the side wall. This embodiment permits the realisation of a circumferential aeration gap between dish and lid. The circumferential aeration gap can be realised uniformly in particular.

Preferably, the means for holding have at least three supporting elements, so that the lid can be held in a stable arrangement on the dish. Preferably, the means for holding have a number of supporting elements that can be divide by 2. The means for holding have preferably four supporting elements. The supporting elements are preferably disposed as being uniformly distributed over the perimeter of the cell culture dish.

According to a further embodiment, there is a first pair of resilient supporting elements on two opposing sections of the side wall, and a second pair of resilient supporting elements on two additional opposing sections of the side wall, the second pair being offset with respect to the first pair about approximately 90°. In this way, a cell culture dish having a rectangular, oblong or circular bottom surface may be realised in particular.

The resilient supporting element can be realised as a destroyable and/or fictile supporting element in particular. In these embodiments, the lid arrives in the sealing position from out the aeration position by destruction or plastic deformation of the resilient supporting element. These embodiments are taken into consideration in particular for cell culture dishes which are provided for one-time aeration of a cell culture or of micro-organisms, because after these cell culture dishes have been sealingly closed once, the supporting element permitting the aeration is destroyed or deformed, and thus no more usable.

In a preferred embodiment, the resilient supporting element is elastic. In this embodiment, the lid can be brought into the sealing position from out the aeration position—in the latter, the lid lays slackly on the supporting element with its lid side wall—by overcoming elastic restoring forces, and also back into the aeration position again from out the sealing position. When taking off the lid, the resilient supporting element returns into its starting position, so that the lid can be slackly put on the supporting element anew. This embodiment permits repeated opening, aeration and sealing closure of the cell culture dish, as this is usual in cell technology investigations extending over several days. Thus, this embodiment is particularly suited for cell culture dishes which are taken out of the incubator after an incubation or cultivation, respectively, in order to examine the cell culture or micro-organisms under the microscope or to add a medium, and which are subsequently put into the incubator anew for further incubation or cultivation, respectively, wherein this treatment can be repeated plural times if need be. Before taking it out of the incubator, the lid is brought into the sealing position, in order to preserve the $CO_2$-enriched atmosphere within the cell culture dish and to prevent swashing over and leaking out of the culture medium during the transportation; and before putting it back into the incubator for further incubation, the lid is brought into the aeration position. According to this embodiment, the cell culture dish may be realised as a single-use article, made of plastic material in particular.

According to a further embodiment, the resilient supporting element comprises a spring tongue.

According to one embodiment, the dish has a gripping edge that projects outwardly from the side wall. The gripping edge permits in particular the easy manual and/or automatic treatment of the cell culture dish. The gripping edge may extend over one or several perimeter sections of the side wall of the dish. It may also extend continuously or over the entire perimeter of the side wall. The gripping edge facilitates holding or transportation, respectively, of the dish. According to one embodiment, the resilient supporting element is a section of the gripping edge. The resilient supporting element is preferably a spring tongue, which forms a section of the gripping edge. In its unloaded condition, the spring tongue may be oriented in an acute angle towards the bottom wall, so that it is swivelled nearer to the bottom wall when the lid is displaced from the aeration position to the sealing position. According to one embodiment, the spring tongue is fixedly connected to the side wall at one end, extends in parallel to the bottom wall and has a projection projecting towards the lid on the other end, onto which the lid side wall is adapted to be put. In this embodiment, the spring tongue can be a part of an annularly circulating gripping edge of the dish. It is possible to swivel the spring tongue nearer to the bottom wall without that the unloaded spring tongue is directed towards the bottom wall in an acute angle.

The projection of the spring tongue can be used to clamp the lid into a gap between the projection and the side wall of the dish at the lower edge of the lid side wall, the lid being aligned in an acute angle to the dish. In this inclined position of the lid there is an aeration gap between lid and dish, whose width increases in the perimeter direction of the dish starting from the projection up to a position situated opposite to the projection, on both sides of the projection indeed. This further aeration position ensures a gas exchange with the surroundings that is enhanced with respect to the aeration position wherein the lid is held by the means for holding. This may be desired when the cell culture dish populated with cells is put back into the incubator after a longer period outside the incubator, in order to ensure a fast acclimatisation to the atmosphere prevailing there. In the further aeration position, the dish remains to be covered up and protected against contaminations. The lid is still securely held by the dish, and even in this position, it has contact only with the dish, that is to say it does not touch the incubator itself, e.g. Thus, the contamination risk is minimised even in this position. For securely holding the lid in the further aeration position, the lid side wall can be equipped with a circulating edge flange projecting radially outwardly at the outer side, and/or the projection may have a clamping projection that projects radially towards the inside.

In order to lock the lid in the further aeration position with orientation of the lid in an acute angle to the dish, particular differently realised holding elements may be provided also, which do not have any additional function like the supporting elements. These holding elements may have a projection that projects upwardly in a distance from the side wall in a hook-like fashion, so that the lid side wall can be clamped in a tilted position between the projection and the side wall of the dish.

According to one embodiment, the at least one elastic supporting element is formed on the lid. Preferably, the at least one elastic supporting element is formed on a lid side wall. In this, it is dealt for instance with a section of the lid side wall which is realised as a spring tongue which can be deflected vertically to the perimeter of the lid side wall. The spring tongue can be limited by parallel slots of the lid side wall that emanate from the lower edge of the lid side wall. On the inside perimeter, the spring tongue can sit close to a ramp-like or wedge-like projection on the perimeter of the side wall of the dish. As a consequence, the spring tongue slips over the ramp when the lid is pressed against the dish, and is increasingly deflected by this.

The lid and the dish may have means for sealing which make sure that the lid sits sealingly on the side wall in the sealing position. For this purpose, the contact surfaces of lid and side wall can be shaped in a particular fashion so as to be sealing seats. The contact surfaces can be made to be particularly well-matching in this. According to a preferred embodiment, the means for sealing have an undercut that circulates on the outer side of the side wall in the perimeter direction, and a sealing region projecting inwardly, which circulates on the inner side of the lid side wall in the perimeter direction, the projecting sealing region gripping behind the undercut in the sealing position, and being out of engagement with the undercut in the aeration position. Thus, a positively fitting connection is produced in the sealing position. According to a preferred embodiment, in the sealing position, a conical section on the inside perimeter of the circumferential lid side wall sits sealingly close to the curved surface of the side wall of the dish, and/or a conical section on the curved surface of the side wall sits sealingly close to the inside perimeter of the circumferential lid side wall. A particularly high pressing force per unit area, and accordingly an enhanced sealing effect, is achieved in the region of the undercut and the projecting sealing region of the first embodiment, and of the conical section of the second embodiment.

According to a preferred embodiment, there are means for detachably holding the lid on the dish in the sealing position. By this, the lid is secured on the dish in the sealing position.

For instance, the means for detachably holding are frictionally fitting means or catch means. The frictionally fitting means may be formed by sealing seats on lid and dish, which co-operate in the sealing position. Catch means can be formed by the undercut and the projecting sealing region co-operating with it, the projecting sealing region being caught behind the undercut.

The described means for detachably holding, the catch means in particular, can be easily overcome by pressing the lid together on two diametrically opposing sides. The pressing together results in a deformation of the lid (for instance, the originally circular lid is ovally deformed for a short time), a lever action begins which facilitates the release of the lid from the dish. Such a compression may also be performed by one single hand, so that the user can easily detach the lid from the cell culture dish without having to pull on the dish. As soon as the compression is ended, the lid reverts into its original shape. By this kind of detachment, it is avoided that turbulences arise in the cell culture medium in the cell culture dish that is filled with cell culture medium and populated by cells, which turbulences may be disadvantageous for the cells on the one hand, and on the other hand may lead to drizzle-like droplet/aerosol formation of the cell culture medium, to which the user would be exposed and which might lead to impairment of his/her health.

The cell culture dish of the present invention is essentially made of plastic material. Suitable plastic materials are selected from the group consisting of transparent plastic materials like polystyrene (PS), polypropylene (PP), polymethylpentene, polycarbonate (PC), polymethylmethacrylate (PMMA), polymethylacrylmethylimide (PMMI) and cycloolefine copolymer (COC), as well as of mixtures and/or copolymers of at least two of these plastic materials. According to one embodiment, the dish and/or the lid is made of at least one plastic material. The same or different plastic materials may be used for dish and lid. Moreover, dish and/or lid can consist of plural plastic materials. For instance, the lid may have an inserted or injected sealing ring on the inside perimeter of the lid side wall, which forms means for sealing together with a sealing surface that circulates on the outside perimeter of the side wall of the dish. A further example for a dish and/or lid consisting of plural plastic materials is a cell culture dish which features a particularly transparent and/or reflection-free plastic region in at least one selected region of the dish and/or the lid. Thus, it is possible to form regions which are particularly suited for the optical observation of the cells.

Lid and plastic material are preferably of the same material. A preferred material is polystyrene for instance.

Further preferred, dish and/or lid are at least in regions made of a highly transparent plastic material like PMMA, PMMI and/or COC. Lid and dish are preferably transparent in the region of the bottoms. Further preferred they are entirely transparent. A transparent plastic material permits optical examination of cultures which are disposed in the cell culture dish without having to open the cell culture dish. For this purpose, the cell culture dish is entirely or partly made of a plastic material that is as clear as glass.

Furthermore, the cell culture dish of the present invention may feature surface modifications, which support the binding and the growth of cells. Such surface modifications are preferred in particular which are applied by plasma modification.

BRIEF DESCRIPTION OF EACH OF THE
FIGURES OF THE DRAWINGS

Figure 4:
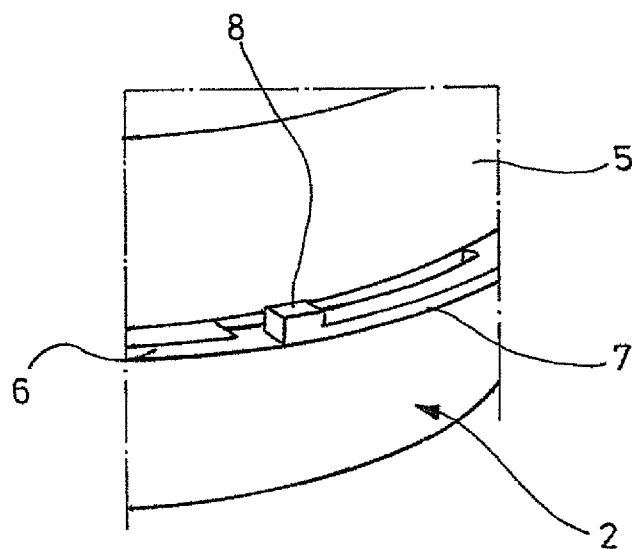
Figure 5:
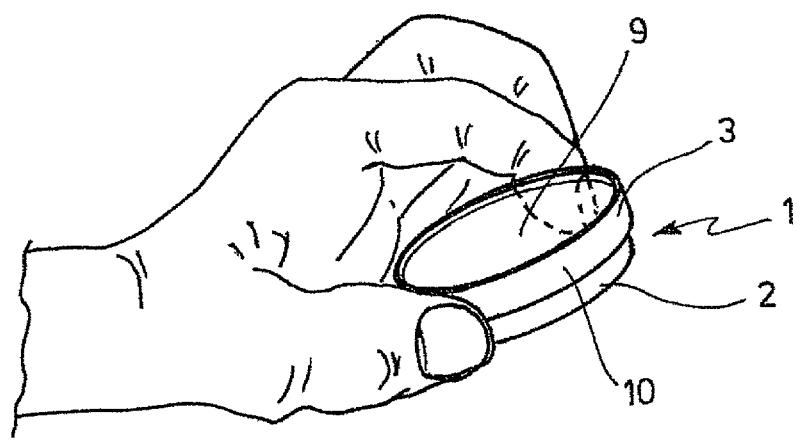
Figure 6:
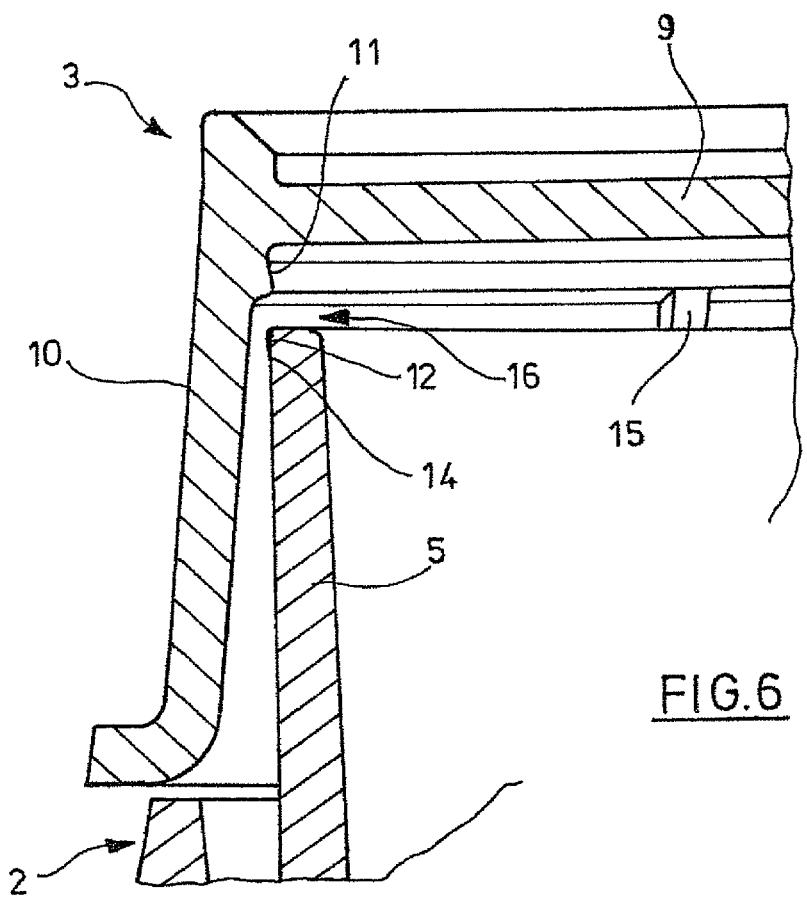
Figure 7:
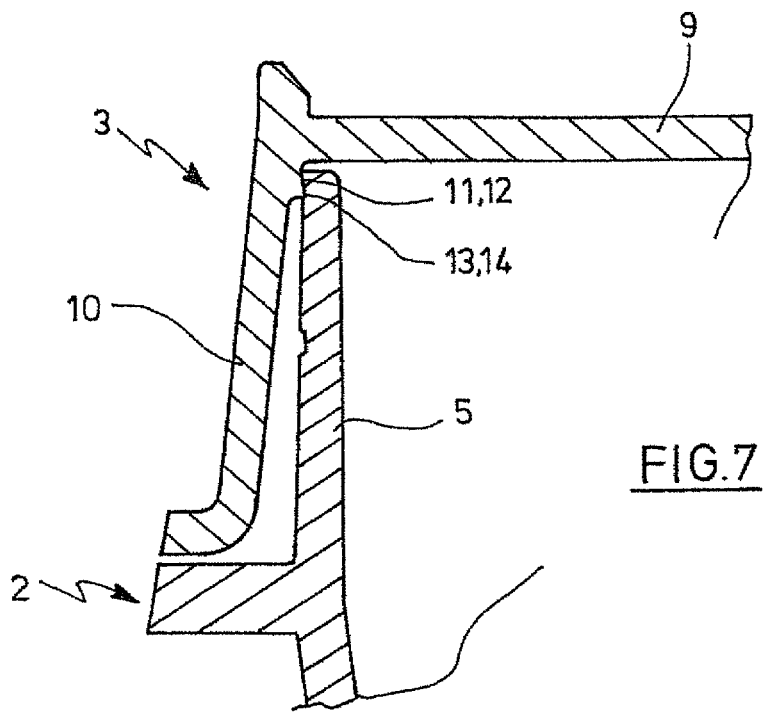
Figure 8:
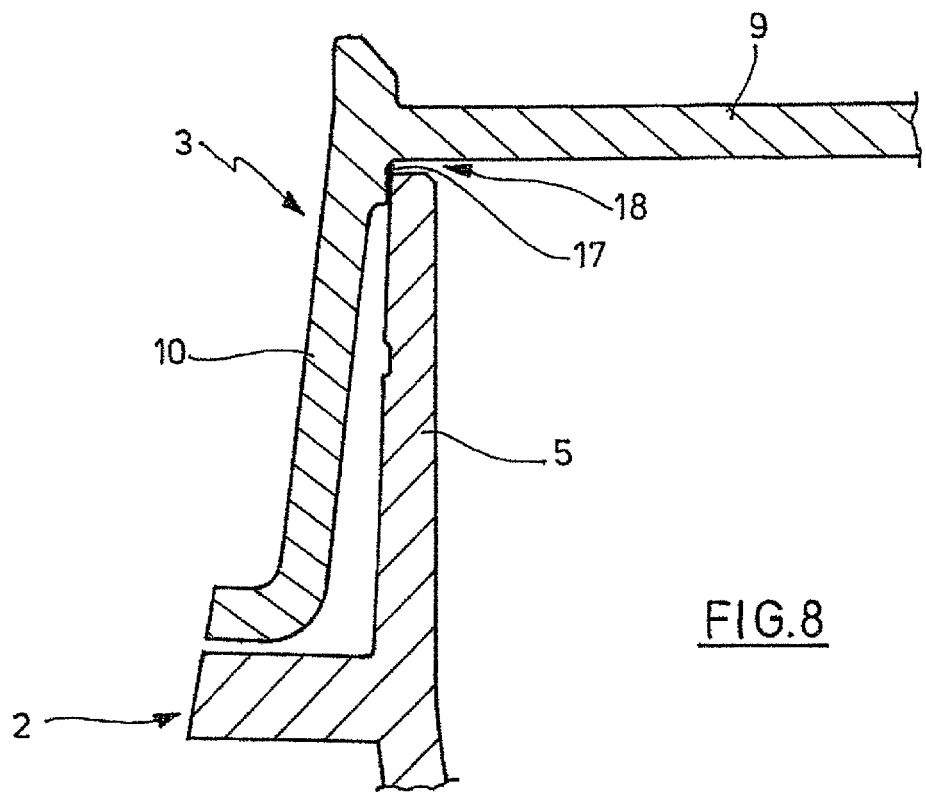
Figure 9:
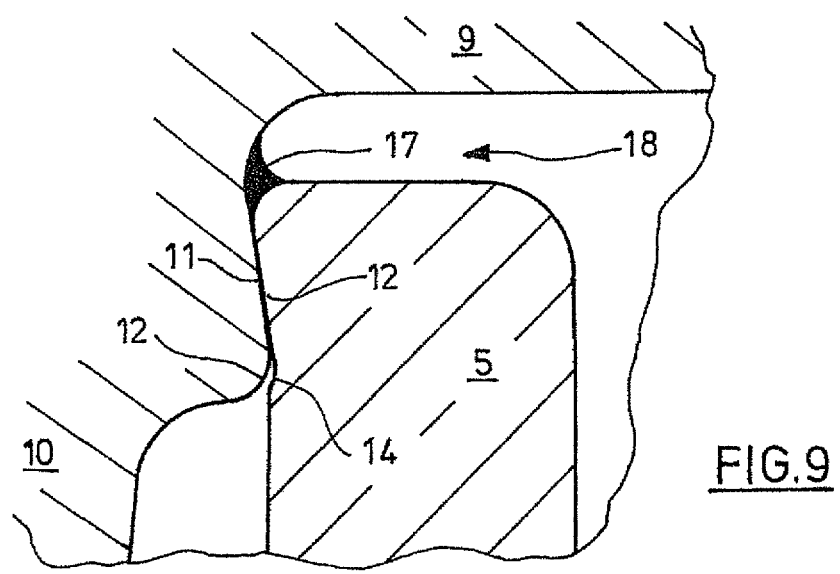
Figure 10:
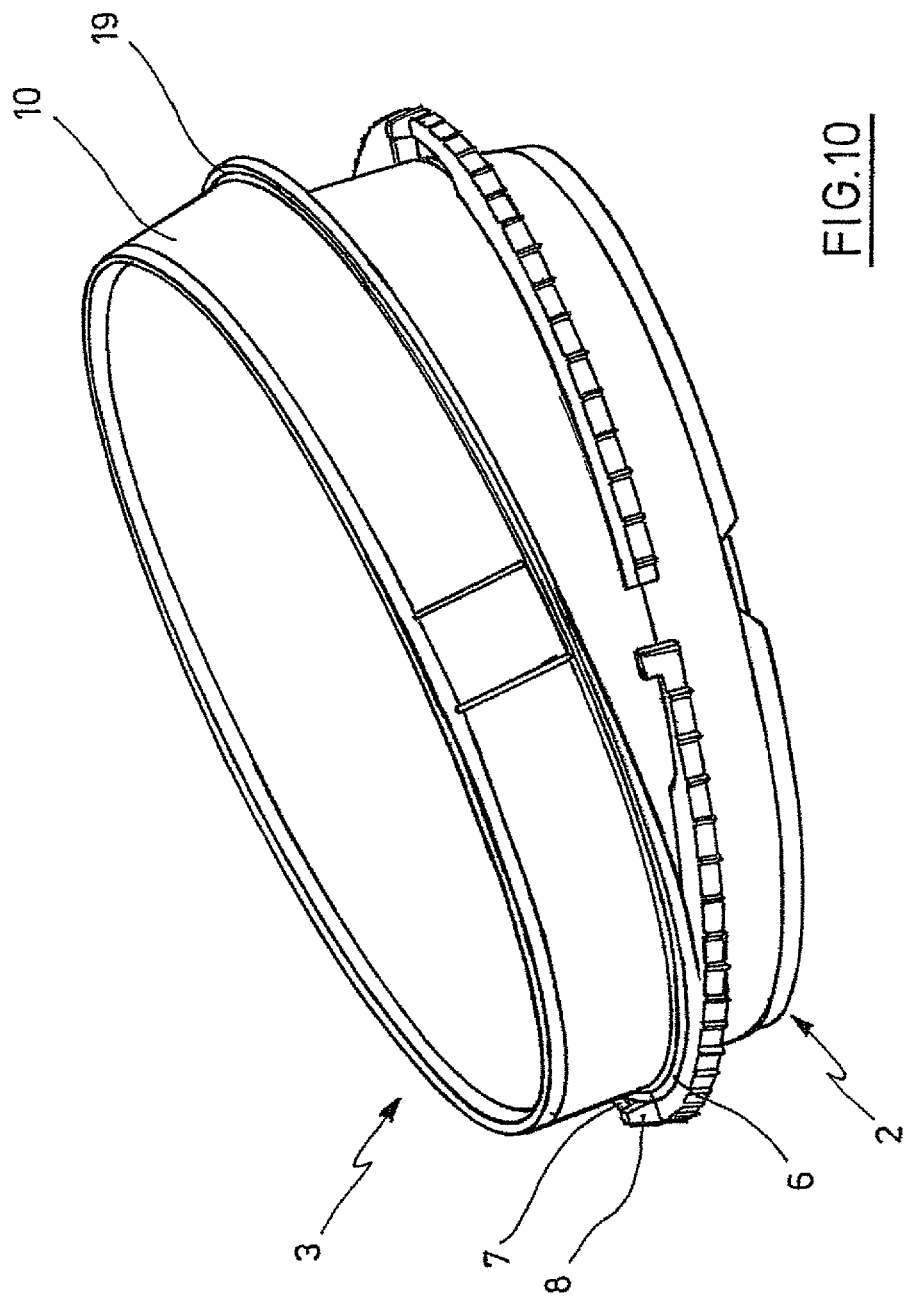
Figure 11:
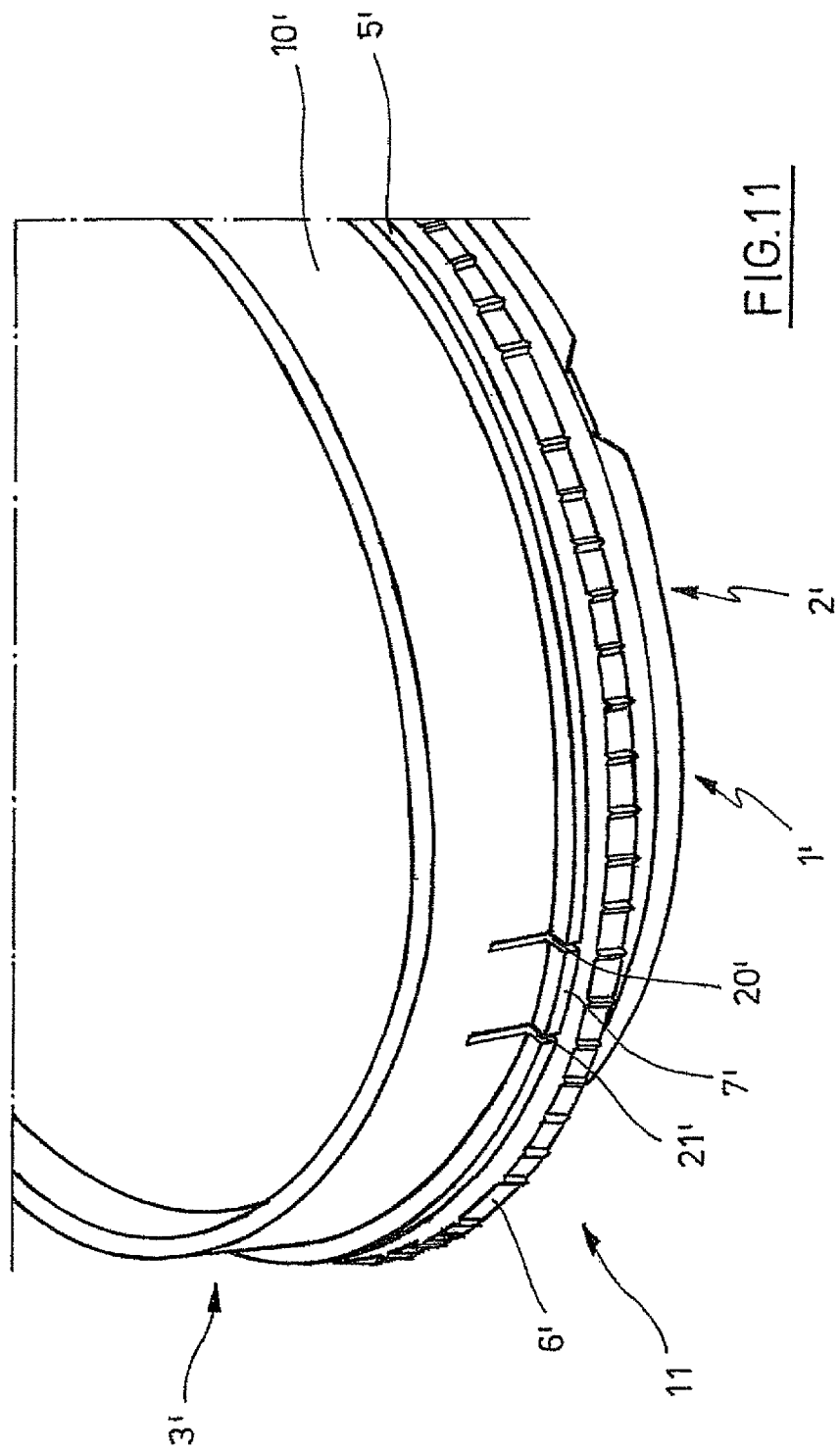

The present invention is explained in more detail by means of the attached drawings of an example of its realisation. In the drawings show:

FIG. 1 a cell culture dish in the aeration position, in a partially cut perspective view;

FIG. 2 the same cell culture dish in the sealing position, in a partially cut perspective view;

FIG. 3 the same cell culture dish in a view from the downside;

FIG. 4 the dish of the same cell culture dish in a partial, perspective side view;

FIG. 5 the same cell culture dish when opening the lid, in a perspective view slantly from the side;

FIG. 6 the same cell culture dish in the aeration position, in an enlarged vertical partial section;

FIG. 7 the same cell culture dish in the sealing position, in an enlarged vertical partial section;

FIG. 8 the same cell culture dish in the sealing position with a sealing wedge of liquid, in an enlarged vertical partial section;

FIG. 9 the sealing wedge of liquid in a further enlarged vertical partial section;

FIG. 10 the same cell culture dish in a further aeration position, with lid set inclinedly in a perspective view slantly from the side;

FIG. 11 a further embodiment of the cell culture dish with spring tongues integrated into the lid side wall, in an enlarged perspective view slantly from the upside and from the side.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated In the present application, the designations "up" and "down" refer to an alignment of the cell culture dish wherein the dish rests on a horizontal support with its bottom.

Same reference signs are used for corresponding features in the explanation of different realisation examples, and different peculiarities of a further realisation example are designated by a superscript (').

The cell culture dish 1 comprises a dish 2 and a lid 3, each having a circular bottom area. The dish 2 has a bottom wall 4, from which a circumferential side wall stands upwardly.

An essentially annular circumferential gripping edge 6 projects towards the outside on the outer side of the side wall 5, at about half the height thereof. The gripping edge 6 comprises four spring tongues 7, which are uniformly distributed over the perimeter of the dish 2. On their solid end, the spring tongues 7 are one-piece connected to the gripping edge 6 and extend essentially in the plane of the gripping edge 6. On their free end, they have a projection 8 or notches, respectively, projecting upward from the remainder of the gripping edge 6.

The gripping edge 6 is interrupted in regions where the spring tongues 7 are arranged. It is also possible to realise the gripping edge 6 in an uninterrupted fashion, wherein the spring tongues 7 can be limited by slots that are disposed in the gripping edge 6.

The lid 3 has a covering wall 9. A circumferential lid side wall 10 projects downward from the edge of the covering wall 9.

On the inside perimeter of the lid side wall 10 there is a conical section 11, which forms a sealing seat of the lid 3. A circumferential conical section 12 on the outer perimeter of the side wall 5 is associated to the conical section 11.

According to FIGS. 6 to 8, the conical section 11 is disposed on a projecting sealing region 13 circulating on the inside perimeter of the lid side wall 10. The conical section 12 is disposed on an undercut 14 at the outer perimeter of the side wall 5.

The conical section 11 and the conical section 12 each enlarge towards the covering wall 9.

The outer diameter on the upper end of the side wall 5 is about 0.1 to 0.3 mm greater than the inside diameter of the lid side wall 10 on the lower end of the projecting sealing region 13. The difference is preferably about 0.15 mm.

The undercut 14 has a depth of about 0.01 to 0.05 mm. The depth is preferably 0.03 mm.

By way of example, the conical section 11 and the associated conical section 12 may have a height of 0.3 mm-1.55 mm, preferably 0.5 mm-1 mm and most preferably a height of 0.5 mm.

The lid 3 has wedge-shaped ribs 15 on the inside perimeter of the lid side wall 10, which extend up to the lower edge of the projecting sealing region 13. This is shown in FIG. 6 only.

The ribs 15 are wedge-shaped, their height increasing towards the upside to the projecting sealing region 13. The lower end of the ribs 15 is arranged in a distance to the projecting sealing region 13, which corresponds to about one third or half the height of the lid side wall 10. The ribs 15 centre the lid 3 on the dish 2 and thus they facilitate the catching.

Several ribs 15 are uniformly distributed over the inside perimeter of the lid side wall 10. Preferably there are at least three ribs 15. In the example there are six ribs 15, only one being shown however.

Dish 2 and lid 3 can be made such that they essentially coincide with known cell culture dishes in their inner and outer dimensions. In particular, the inside diameter of the side wall 5 may be in the range of 30 to 150 mm, for instance at 55 mm. The height of the side wall 5 may be in the range of 5 to 20 mm; for instance it may be 15 mm.

Dish 2 and lid 3 are made of polystyrene for instance.

When the lid 3 is slackly put onto the dish 2 according to FIGS. 1 and 6, such that the lower edge of the lid side wall 10 lays on the projections 8, there is an aeration gap between dish 2 and lid 3. The height of the aeration gap is in a range of 0.1 mm-1 mm, preferably 0.3 mm-0.7 mm and particularly preferably at 0.5 mm. Putting up the lid 3 onto the dish 2 in the aeration position may be performed easily by one single hand.

According to FIGS. 2 and 7, the lid 3 can be brought into the sealing position by pressing against the dish 2. In this, the lower edge of the lid side wall 10 deflects the spring tongues 7 somewhat downward. The side wall 5 slips over the ribs 15 with its upper edge, and is centred through this. At the same time, the side wall 5 is radially somewhat compressed, and the lid side wall 10 is radially somewhat widened. Finally, the projecting sealing region 13 snaps below the undercut 14, and the conical regions 11, 12 sit sealingly close to each other. As a consequence, the dish 2 is tightly closed by the lid 3. In this position, the lid 3 is fixed on the dish 2 by the positive engagement of undercut 14 and projecting sealing region 13. The sealing is effected by the clamping force between the sections 11, 12. Thus, there is a positive as well as a frictional connection in the sealing position. By this combination, there is a safe, in particular liquid-tight capping, which may be released easily again however, namely by pressing the lid side wall 10 together (lever forces occur in this).

For additional sealing, a wedge of liquid 17 can be brought between the upper edge of the side wall 5 and the upper end of the lid side wall 10 according to FIGS. 8 and 9. For this purpose, there is a small circumferential remaining gap between the side wall 5 and the covering wall 9. The sealing between dish 2 and lid 3 is enhanced by the wedge of liquid 18.

According to FIG. 5, the cell culture dish is opened by laterally pressing against the lower circular edge of the lid side wall 10 with index finger and thumb, so that it deforms itself to an ellipse. This has the consequence that the flat covering wall 9 and the conical section 11 of the lid side wall 10 are deformed. In the region situated at 90° to the force direction of the fingers, the engagement of the projection 13 in the undercut 14 is ended as a consequence of this, and the lid 3 is detached from the dish 2.

The cell culture dish 1 of the present invention has better utilisation properties than conventional cell culture dishes. In particular, dish 2 and lid 3 can easily be connected to each other. Taking on and off the lid 3 is possible with only one single hand. The cell culture dish is sealingly closed in the sealing position, so that the $CO_2$ content in the interior of the cell culture dish 1 can be kept almost constant. Swashing over through an aeration gap, which exists when a lid is merely put up, can no more occur when the lid closes the dish sealingly. The aeration position and the sealing position can be utilised in their full extent without influencing the respective other position.

According to FIG. 10, the lid 3 can be kept in a further aeration position on the dish 2, wherein the lid 3 is aligned to the dish 2 at an acute angle. For this purpose, a circumferential outwardly projecting edge flange 19 of the lid 3 is put against the inner side of the projection 8 of a spring tongue 7. The edge flange 19 is clamped into the gap between the projection 8 and the side wall 5, due to which the lid 3 is fixed in the shown alignment. In this further position, a strongly widening aeration gap is attained, which permits a particularly good gas exchange. But however, the dish 2 is covered up at the topside, even here the lid 3 being merely in contact with the dish 2. In particular, the lid 3 does not touch the subsoil, which may be contaminated, and so it is avoided that contaminations arrive in the dish during the aeration.

The cell culture dish 1' according to FIG. 11 differs from the already mentioned one in that the edge 6 circulates without interruption and has no spring tongues 7. Instead, spring tongues 7' are existing in the lid side wall 10'. For this purpose, the lid side wall 10' has parallel slots 20', 21' emanating from its lower edge, which limit the spring tongues 7'. In the example, three spring tongues 7' are distributed over the perimeter of the lid side wall 10', only one thereof being shown.

The spring tongues 7' have not shown guide cams projecting towards the inside. The guide cams of the spring tongues 7' are guided on not shown guide surfaces on the lower part of the side wall 5' which laterally project like wedges or beads. The guide surfaces may run in an arbitrary manner, for instance they may circulate entirely or even circulate with interruptions. When the lid 3' is put up slackly, the spring tongues 7' are supported on the not shown wedge surfaces in elevated positions with respect to the dish 2'. When pressing lid 3' and dish 2' together, the spring tongues 7' slip on the guide surfaces and are deflected towards the outside. Finally, the projecting sealing region 13' snaps behind the undercut 14', and the lid 3' is sealingly fixed on the dish 2' in the sealing position.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:
1. A cell culture dish, comprising:
a dish (2) with a bottom wall (4) and a circumferential side wall (5) standing upward from the same,
a lid (3), having a lid side wall (10) which in a sealing position sits sealingly on the side wall (5), the lid side wall (10) is extending over the side wall of the dish (4),
contact surfaces of lid (3) and side wall (5) being formed as sealing seat (13, 14) and defining frictionally fitting means, which releasably retains the lid on the dish in the sealing position,
the sealing seat of the lid (3) being formed by a conical section (11) on a projecting sealing region circulating on the inside perimeter of the lid side wall (10) and the sealing seat of the side wall (5) being formed by a circumferential conical section (12) disposed on an undercut (14) on the outer perimeter of the side wall (5),
the side wall (5) of dish (2) has at least one laterally projecting spring tongue (7) onto which a lid side wall (10) in the aeration position of the lid (3) is settable, in the aeration position an aeration gap is formed between the side wall (5) and lid (3),
the conical sections (11, 12) and the undercut (14) being designed such that the sealing position can be achieved by pressing the lid (3) onto dish (2)
whereby the lower edge of the lid side wall (10) deflects the spring tongues (7) in an axial direction, at the same time the side wall (5) is radially somewhat compressed and the lid side wall (10) is radially somewhat widened and finally the projecting sealing region (13) is snapped below the undercut (14) and the conical sections (11, 12) sit sealingly close to each other in the sealing position,
wherein the sealing is effected by a clamping force between the undercut (14) and the projecting sealing region (13), and further wherein the at least one spring tongue (7) does not have a holding function in the sealing position, and
the side wall of the lid being designed such that the lid side wall can be compressed from opposing sides by a single or one hand operation so that the lid side wall (10) deforms itself to an ellipse whereby the engagement of the projecting sealing region (13) is ended in a consequence of this and the lid (3) is detachable from the dish (2).

2. A cell culture dish according to claim 1, wherein the dish (2) has at least three resilient supporting elements (7).

3. A cell culture dish according to claim 1, wherein the dish (2) has resilient supporting elements (7) on opposing sections of the side wall (5).

4. A cell culture dish according to claim 3, featuring a first pair of resilient supporting elements (7) on two opposing sections of the side wall (5), and a second pair of resilient supporting elements (7) on two additional opposing sections of the side wall (5), the second pair being offset with respect to the first pair about approximately 90°.

5. A cell culture dish according to claim 4, wherein the spring tongue (7) is fixedly connected to the side wall (5) at one end, extends in parallel to the bottom wall (4) and has a projection (8) projecting towards the lid (3) on the other end, onto which the lid side wall (10) is adapted to be put.

6. A cell culture dish according to claim 1, featuring a gripping edge (6) that projects from the side wall (5) at the outer side.

7. A cell culture dish according to claim 6, wherein the resilient supporting element (7) is a section of the gripping edge (6).

8. A cell culture dish according to claim 7, wherein the undercut (14) circulates on the outer side of the side wall (5), and a sealing region (13) projects on the inner side of the lid side wall (10), the projecting sealing region (13) gripping behind the undercut (14) in the sealing position, and being out of engagement with the undercut (14) in the aeration position.

9. A cell culture dish according to claim 1, wherein in the sealing position, a conical section (11) on the inside perimeter of the circumferential lid side wall (10) sits sealingly close to the curved surface of the side wall (5) of the dish (2), and/or a conical section on the curved surface of the side wall (5) sits sealingly close to the inside perimeter of the circumferential lid side wall (10).

10. A cell culture dish according to claim 1, with a dish (3) made of plastic material, and/or a lid (2) made of plastic material.

11. A cell culture dish, comprising:
   a dish (2) with a bottom wall (4) and a circumferential side wall (5) standing upward from the same;
   a lid (3) having a lid side wall (10) which in a sealing position sits sealingly on the side wall the lid side wall (10) is extending over the side wall of the dish (4);
   contact surfaces of lid (3) and side wall (5) being formed as sealing seat (13, 14) and defining frictionally fitting means, which releasably retains the lid on the dish in the sealing position;
   the sealing seat (13) of the lid (3) being formed by a conical section (11) on a projecting sealing region (13) circulating on the inside perimeter of the lid side wall (10) and the sealing seat of the side wall (5) being formed by a circumferential conical section (12) disposed on an undercut (14) on the outer perimeter of the side wall (5);
   the lid (3) has at least one spring tongue which is formed by parallel slits in the lid side wall (10) starting from the lower edge of the lid side wall (10), the spring tongue being deflectable perpendicular to the circumference of side wall (10), the inner circumference of the tongue engaging a ramp-like or wedge-like projection on the circumference of a side wall of dish (2);
   the conical sections (11, 12) and the undercut (14) being designed such that the sealing position can be achieved by pressing the lid (3) onto dish (2) whereby the lower edge of the lid side wall (10) deflects the spring tongues (7) in an axial direction, at the same time the side wall (5) is radially somewhat compressed and the lid side wall (10) is radially somewhat widened and finally the projecting sealing region (13) is snapped below the undercut (14) and the conical sections (11, 12) sit sealingly close to each other in the sealing position,
   wherein the sealing is effected by a clamping force between the undercut (14) and the projecting sealing region (13), and further wherein the at least one spring tongue (7) does not have a holding function in the sealing position, and
   and the side wall of the lid being designed such that the lid side wall can be compressed from opposing sides by a single or one hand operation so that the lid side wall (10) deforms itself to an ellipse whereby the engagement of the projecting sealing region (13) is ended in a consequence of this and the lid (3) is detachable from the dish (2).

* * * * *